United States Patent [19]

de Heij et al.

[11] 3,959,388

[45] May 25, 1976

[54] PREPARATION OF PHLOROGLUCINOL OR ITS MONOMETHYL ETHER

[75] Inventors: Nicolaas A. de Heij, Blerick; Andreas J. J. Hendrickx, Venlo, both of Netherlands

[73] Assignee: Andeno B.V., Venlo, Netherlands

[22] Filed: Dec. 12, 1973

[21] Appl. No.: 424,178

Related U.S. Application Data

[63] Continuation-in-part of Ser. No. 272,928, June 23, 1972.

[52] U.S. Cl. .............................. 260/613 D; 260/629
[51] Int. Cl.² ...................... C07C 43/20; C07C 37/02
[58] Field of Search ........................ 260/629, 613 D

[56] References Cited
UNITED STATES PATENTS 3,778,481   12/1973   Biller et al. .................... 260/629

FOREIGN PATENTS OR APPLICATIONS 1,588,584   4/1970   France ......................... 260/629
834,254     5/1960   United Kingdom ............ 260/629

*Primary Examiner*—Bernard Helfin
*Attorney, Agent, or Firm*—Albert C. Johnston

[57] ABSTRACT

Phloroglucinol or its monomethyl ether is prepared at high yield, without producing by-product pollutants, by reacting a phenol that contains one or more leaving groups, e.g. a halogen atom, with alkali metal hydroxide in the initial absence of water in an inert organic liquid medium, e.g. pseudocumene, which forms an azeotrope with water formed by the reaction; distilling off reaction water as azeotrope; and acidifying the resulting alkali metal salt.

10 Claims, No Drawings

PREPARATION OF PHLOROGLUCINOL OR ITS MONOMETHYL ETHER

This application is a continuation in part of our copending application Ser. No. 272,928 filed June 23, 1972.

This invention relates to a method of preparing phloroglucinol (s-trihydroxy benzene) or its monomethyl ether and to such compounds so prepared.

Phloroglucinol is a well-known and versatile compound. It is used, for instance, as a coupling agent in diazotype copying processes and as an intermediate in the preparation of certain drugs. For the latter purpose phloroglucinol ethers are also useful.

Hitherto, phloroglucinol has been manufactured mainly by oxidation of the hazardous explosive TNT (trinitrotoluene) to 2,4,6-trinitrobenzoic acid, followed by reduction to the corresponding triamino compound, decarboxylation and hydrolysis. This method of manufacture suffers from several disadvantages one of them being the relatively low overall yield, which is due inter alia to the many reaction steps. Another disadvantage, particularly important nowadays, is that the reaction produces a large amount of worthless byproducts, some of which may present hazards to public health and may add to air, soil and water pollution. Indeed, because the oxidation of TNT is usually carried out with a sulfuric acid-dichromate mixture, chromic salts and sulfuric acid are usually formed in large amounts as noxious waste products.

Phloroglucinol monoethers are generally prepared by reacting phloroglucinol with an etherifying agent such as an alkyl halide, a dialkyl sulphate or an alcohol.

The object of the present invention is to provide a process for preparing phloroglucinol or its monomethyl ether, which is effective with a minimum of risk of evironmental pollution, avoids the use of the hazardous explosive TNT as starting material, and enables high overall yields. By avoiding the formation of by-products having no economic value, the present invention enables a more economical production of phloroglucinol and its monomethyl ether.

A process meeting the above requirements to a high degree is set forth in our aforesaid copending application Ser. No. 272,928, the disclosure of which is hereby incorporated herein by reference. According to that disclosure, phloroglucinol or its monomethyl ether is prepared by a process which comprises reacting with a proton abstracting agent of sufficient strength to form an yne bond, at an elevated temperature in the presence of an amount of water at least sufficient to monohydrate the or each yne bond formed, a phenol of the formula:

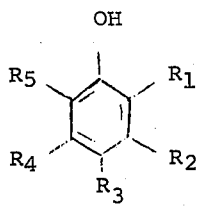

wherein:
$R_1$, $R_3$, $R_4$ and $R_5$, which may be the same or different, each represents a hydrogen atom or a leaving group (as herein defined); and
$R_2$ represents a hydrogen atom, a leaving group or a group of the formula —$OR_6$, wherein $R_6$ represents a hydrogen atom or a methyl group.
with the proviso that:
  i. where $R_2$ represents a leaving group or a group of the formula —$OR_6$, $R_1$ represents a hydrogen atom and only one of $R_3$, $R_4$ and $R_5$ represents a leaving group; and that
  ii. where $R_2$ represents a hydrogen atom, two of $R_1$, $R_3$, $R_4$ and $R_5$ represent leaving groups occupying positions such that, upon leaving, one yne bond can be formed at the 2,3- or the 3,4-position and yne bond can be formed at the 4,5- or the 5,6-position.

That process not only reduces the total amount of waste products to one-tenth of that previously produced but also sulfuric acid and chromic salts - the two biggest water contaminants in the main prior art method - no longer occur as by-products.

The present invention is an improvement in and modification of that process, which reduces the required amount of proton abstracting agent to give a still more economical process.

According to the present invention, there is provided a process for the preparation of phloroglucinol or its monomethyl ether, which process comprises:

1. reacting with an alkali metal hydroxide, suitably lithium, sodium or potassium hydroxide or a mixture of alkali metal hydroxides, in the initial absence of water, in an inert organic liquid medium which forms an azeotrope with water, a phenol of the formula:

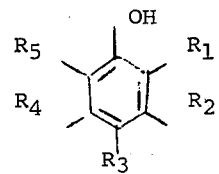

wherein:
$R_1$, $R_3$, $R_4$ and $R_5$, which may be the same or different, each represent a hydrogen atom or a leaving group (as herein defined); and
$R_2$ represents a hydrogen atom, a leaving group or a group of the formula —$OR_6$, wherein $R_6$ represents a hydrogen atom or a methyl group,
with the proviso that:
  i. where $R_2$ represents a leaving group or a group of the formula —$OR_6$, $R_1$ represents a hydrogen atom and only one of $R_3$, $R_4$ and $R_5$ represents a leaving group; and that
  ii. where $R_2$ represents a hydrogen atom, two of $R_1$, $R_3$, $R_4$ and $R_5$ represents leaving groups occupying positions such that, upon leaving, one yne bond can be formed at the 2,3- or the 3.4-position and one yne bond can be formed at the 4,5- or the 5,6-position;

2. distilling off, as azeotrope, water produced by the reaction; and 3. acidifying the alkali metal salt of the trihydroxybenzene, or of its monomethyl ether, so formed to produce the corresponding free tri-hydroxybenzene or monomethyl ether.

By "leaving group" is meant herein any nucleophilic species weaker than —OH or —$OCH_3$, for example a halogen atom. Preferably, the leaving group is a chlorine atom.

As will be evident, the process of the present invention differs specifically from that of the said copending application by utilizing in an initially anhydrous system an inert organic liquid medium that forms an azeotropic mixture with water liberated during the reaction. Examples of suitable inert organic liquid media are toluene, xylene, cymene, pseudocumene, diphenyl ether, Shellsoll T or mixtures thereof. Preferably solvents or mixtures thereof having a boiling point in the range between 130° and 180°C are chosen. Pseudocumene is a very useful solvent, because its boiling point of about 170° C corresponds to an optimum reaction temperature.

Preferably the molar ratio of the alkali metal hydroxide to the phenolic reagent is between 3:1 and 15:1; more specifically between 5:1 and 12:1.

Reaction temperatures as high as 300° C could be used and would favor a high reaction velocity; however, it is preferred to apply relatively moderate temperatures, i.e. temperatures between 130° and 180° C, as aromatic polyhydroxy compounds are readily oxidized in alkaline media at temperatures above 180° C. Preferably the reaction temperature is about 170° C.

Starting with 4-chlororesorcinol, which is commercially available, phloroglucinol can readily be produced by the present process in overall yields of 50% to 70%. To prepare the monomethyl ether, 4-chloro-3-methoxy phenol can be used. The substituent chlorine atom may also be in one of the two other suitable positions, i.e. the 5- or 6-position; and also one of the other halogens may be employed instead of chlorine. Useful starting compounds for preparing phloroglucinol are thus 4-chlororesorcinol, 5-chlororesorcinol, 4-bromoresorcinol, 5-bromoresorcinol; and for preparing phloroglucinol monomethyl ether and 4-chloro-3-methoxyphenol, 6-chloro-3-methoxyphenol, 4-bromo-3-methoxyphenol, 5-bromo-3-methoxyphenol and 6-bromo-3-methoxyphenol.

As starting materials those compounds are preferred in which a chlorine atom is present in the o-position relative to a hydroxyl group.

Instead of the dihydroxybenzene compounds or derivatives thereof mentioned above, monohydroxybenzene compounds can also be converted to phloroglucinol. The monohydroxybenzene compounds must, however, carry the leaving groups at positions such that, upon leaving, one yne bond can be formed at the 2,3-or the 3,4-position, and one yne bond can be formed at the 4,5-or the 5,6-position. When one yne bond is formed at the 3,4-position the other must be formed at the 5,6-position; the combination of two adjacent yne bonds at the 3,4- and 4,5-position is chemically impossible.

Thus, in another preferred method of preparing phloroglucinol according to the invention, for example, 2,6-dichlorophenol dissolved in pseudocumene is heated in the presence of a strong alkali. Of course, instead of the 2,6-dichloro compound, the corresponding phenols having other halogen atoms in the 2-and 6-positions can be used and likewise the halogen atom may be present in other suitable positions such as 2,4- or 2,5-or 3,5-. Generally, any compound that upon reaction results in one of the starting materials mentioned above can also be used as precursor.

The following examples further illustrate practices of the invention.

EXAMPLE 1

144.5 g (1 mole) 4-chlororesorcinol were dissolved in 500 ml of hot (ca. 100° C) pseudocumene.

This solution was added over a period of 2 hours to a stirred refluxing mixture, kept under nitrogen atmosphere, of 423.5 g (6.8 mole) KOH and 800 ml of pseudocumene. The excess of water being liberated was distilled off azeotropically in such a way, that, per unit of time, the quantity of the azeotropic mixture, water plus pseudocumene, being distilled was the same as the quantity of the solution of 4-chlororesorcinol in pseudocumene being added. Consequently the total volume remained constant. At the end of the period of 2 hours about 500 ml of pseudocumene and 45–50 ml of water were distilled.

After another hour of stirring at reflux temperature (169°–170° C) the mixture was permitted to cool slowly to 140° C. Then water was added to dissolve all KCl formed. The resulting mixture was cooled to 40° C and acidified with diluted sulfuric acid to a pH value of 3.5.

An extractant, such as ethyl acetate or methyl ethyl ketone, was added and the precipitated $K_2SO_4$ filtered off. A two layer system resulted from which the organic phase was separated and concentrated by evaporation. Recrystallization of the residue from water gave phloroglucinol in a yield of 67–68%.

The $K_2SO_4$ obtained from the reaction may be collected and sold, thus making the phloroglucinol production more economic.

EXAMPLE 2

A solution of 32.6 g (0.2 mole) 2,6-dichlorophenol in 150 ml hot pseudocumene was added to a stirred, refluxing mixture, kept under nitrogen atmosphere, of 100 g (1.8 mole) KOH and 200 ml pseudocumene. During 4 hours the excess of water being liberated was distilled off azeotropically in such a way that the total volume remained constant.

After another hour of stirring at reflux temperature the mixture was permitted to cool slowly to 140° C, 100 ml water were then added, and the resulting mixture was cooled further to 40° C. After the aqueous layer had been separated it was added to a mixture of 200 ml water and 70 g sulfuric acid (the pH obtained was approximately 3.5).

Ethyl acetate was used as extractant, the precipitated $K_2SO_4$ filtered off, and from the resulting two layer system the organic phase was separated and concentrated by evaporation. Upon recrystallization of the residue from water, phloroglucinol in a yield of 13.6 g (0.11 mole), i.e. 55%, was obtained.

EXAMPLE 3

A solution of 63.4 g (0.43 mole) chlororesorcinol monomethyl ether (mixture of 4- and 6-isomer) in 200 ml hot pseudocumene was added to a stirred, refluxing mixture, kept under nitrogen atmosphere, of 200 g (3.57 mole) KOH and 400 ml pseudocumene. During 4 hours the excess of water being liberated was distilled off azeotropically in such a way that the total volume remained constant.

After another hour of stirring at reflux temperature the mixture was permitted to cool slowly to 140° C, 200 ml water were then added and the resulting mixture was cooled further to 40° C. After the aqueous layer had been separated it was added to a mixture of 280 ml water and 140 g sulfuric acid (the pH obtained was approximately 3.5).

Ethyl acetate was used as extractant, the precipitated $K_2SO_4$ filtered off, and from the resulting two layer system the organic phase was separated and concentrated by evaporation. A residue containing 34 g phloroglucinol monomethyl ether and 12 g phloroglucinol was obtained.

What is claimed is:

1. A process for the preparation of phloroglucinol or its monomethyl ether which comprises:
    1. reacting with alkali metal hydroxide at a temperature between 130° and 180° C in the initial absence of water, in an inert organic liquid medium which forms an azeotrope with water and with said hydroxide present in a molar ratio of between 5:1 and 12:1 to the amount of phenol present, a phenol of the formula:

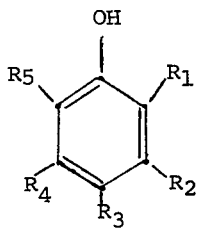

wherein
$R_1$, $R_3$, $R_4$ and $R_5$, which may be the same or different, each represents a hydrogen atom or a halogen atom selected from the group consisting of chlorine and bromine atoms, and
$R_2$ represents a hydrogen atom, a said halogen atom or a group of the formula $-OR_6$, wherein $R_6$ represents a hydrogen atom or a methyl group;
with the proviso that:
    i. when $R_2$ represents a said halogen atom or a group of the formula $-OR_6$, $R_1$ represents a hydrogen atom and only one of $R_3$, $R_4$ and $R_5$ represents a said halogen atom; and that
    ii. when $R_2$ represents a hydrogen atom. two of $R_1$, $R_3$, $R_4$ and $R_5$ each represents a said halogen atom occupying a position on the benzene ring vicinal to at least one position thereon occupied by a hydrogen atom;
    2. distilling off, as azeotrope, water produced by the reaction; and
    3. acidifying the alkali metal salt of the tri-hydroxybenzene or monomethyl ether thereof so formed to produce the corresponding free tri-hydroxybenzene or monomethyl ether.

2. A process according to claim 1 wherein $R_1$ and $R_4$ represent hydrogen atoms; one of $R_3$ and $R_5$ represents a said halogen atom, the other a hydrogen atom; and $R_2$ represents a group of said formula $-OR_6$.

3. A process according to claim 1 wherein $R_1$ and $R_5$, which may be the same or different, each represents a said halogen atom and $R_2$, $R_3$ and $R_4$ represent hydrogen atoms.

4. A process according to claim 1 wherein at least one of the halogen atoms is a chlorine atom.

5. A process according to claim 1 wherein said phenol is 4-chloro resorcinol, 2,6-dichloro phenol or 4- or 6-chloro resorcinol monomethyl ether.

6. A process according to claim 1 wherein the reacting is effected at a temperature of about 170° C.

7. A process according to claim 1 wherein the alkali metal hydroxide is KOH.

8. A process according to claim 1 wherein the inert organic liquid medium is toluene, xylene, cymene, pseudocumene, diphenyl ether, Shellsol T or a mixture thereof.

9. A process according to claim 1 wherein the inert organic liquid medium is pseudocumene.

10. A process for the preparation of phloroglucinol or its monomethyl ether which comprises: ether,
    1. reacting with potassium hydroxide in pseudocumene at a temperature between 130° C and 180° C, in the initial absence of water, a phenol selected from the group consisting of 4-chloro resorcinol, 2,6-dichloro phenol, and 4-chloro and 6-chloro resorcinol monomethyl ethers, with said hydroxide and said phenol present at a molar ratio of between 5:1 and 12:1;
    2. distilling off, as an azeotrope of water and pseudocumene, water produced by the reaction; and
    3. acidifying the resulting alkali metal salt.

* * * * *

UNITED STATES PATENT OFFICE
CERTIFICATE OF CORRECTION

Patent No. 3,959,388          Dated May 25, 1976

Inventor(s) Nicolaas A. De Heij et al.

It is certified that error appears in the above-identified patent and that said Letters Patent are hereby corrected as shown below:

On the Title Page, in the heading following Item [63], insert:

--[30] FOREIGN APPLICATION PRIORITY DATA
         Dec. 18, 1972 United Kingdom......58421/72
         Sept.10, 1973 United Kingdom......42494/73--

Col. 2, line 12, after "and" read --one--.
     Line 54, after "$R_5$" read --represents-- instead of "represent".

*Signed and Sealed this*

Twenty-sixth *Day of* October 1976

[SEAL]

Attest:

RUTH C. MASON
*Attesting Officer*

C. MARSHALL DANN
*Commissioner of Patents and Trademarks*